United States Patent [19]

Ditrich et al.

[11] Patent Number: 5,679,804
[45] Date of Patent: Oct. 21, 1997

[54] PREPARATION OF PHOSPHONIC ESTERS

[75] Inventors: Klaus Ditrich, Gönnheim; Wolfgang Krause, Brühl, both of Germany

[73] Assignee: BASF Aktiengesellschaft, Ludwigshafen, Germany

[21] Appl. No.: 507,911

[22] Filed: Jul. 27, 1995

[30] Foreign Application Priority Data

Jul. 27, 1994 [DE] Germany ............... 44 26 561.1

[51] Int. Cl.$^6$ ................................... C07F 9/06
[52] U.S. Cl. ................................................. 549/221
[58] Field of Search ................................. 549/221

[56] References Cited

U.S. PATENT DOCUMENTS

| | | | |
|---|---|---|---|
| 3,855,360 | 12/1974 | Shim | 260/929 |
| 4,633,005 | 12/1986 | Nalewajek et al. | 558/125 |
| 5,142,084 | 8/1992 | Carter et al. | 558/88 |
| 5,145,972 | 9/1992 | Chabardes | 549/221 |
| 5,177,238 | 1/1993 | Carter et al. | 558/125 |

FOREIGN PATENT DOCUMENTS

| | | |
|---|---|---|
| 2100123 | 7/1993 | Canada . |
| 430 807 | 6/1991 | European Pat. Off. . |
| 579 113 | 1/1994 | European Pat. Off. . |
| 12 14 680 | 2/1964 | Germany . |

OTHER PUBLICATIONS

*J. Org. Chem.*, vol. 304, 1986, pp. 239–243.
Lu et al., *Synthesis*, No. 7, pp. 563–564.
*Chem. Abst.*, vol. 123, No. 7, Aug. 14, 1995, Abst. No. 083728.

Duhamel et al., *Tetrahedron Letters*, vol. 31, No. 22, pp. 3129–3132, 1990.

Michaelis et al., *Ber.*, vol. 31, 1898, pp. 1048.

*Primary Examiner*—Mukund J. Shah
*Assistant Examiner*—Michael Bucknum
*Attorney, Agent, or Firm*—Keil & Weinkauf

[57] ABSTRACT

Phosphonic esters I

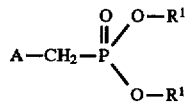

(A is an aromatic radical or an α, β-olefinically unsaturated group and $R^1$ is $C_1$–$C_4$-alkyl or phenyl) are prepared by subjecting a phosphite II

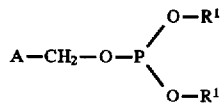

to a rearrangement reaction in the presence of a catalytic amount of a halide ion-donating compound to give I. The compounds I are used as intermediates for organic syntheses, in particular for the synthesis of polyenes.

7 Claims, No Drawings

PREPARATION OF PHOSPHONIC ESTERS

The present invention relates to a process for the preparation of phosphonic esters of the general formula I

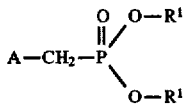

where A is an aromatic radical or an α, β-olefinically unsaturated group and $R^1$ is $C_1$–$C_4$-alkyl or phenyl, from phosphites of the general formula II

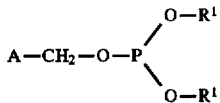

The present invention furthermore relates to a process for the preparation of the phosphonic esters I starting from phosphonites IV, and to some novel phosphonic esters I.

It is known that phosphonic esters of the formula I can be reacted with carbonyl compounds to give olefinically unsaturated compounds in a reaction similar to a Wittig reaction, as described, for example, in Tetrahedron Lett. 31 (1990), 3129. This reaction is used, inter alia, in the synthesis of fine chemicals and active compounds, such as vitamins.

It is known that these compounds have been prepared to date by subjecting trialkyl phosphites and halohydrocarbons to a Michaelis-Arbusov reaction (A. Michaelis, and R. Kaehne, Ber. 31 (1898), 1048). The reaction inevitably produces an equimolar amount of an undesirable alkyl halide. Thus, according to EP-A 430 807, the phosphonic ester can be prepared from the bromine compound

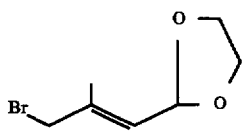

and triethyl phosphite

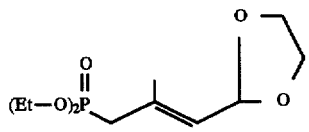

Many attempts have been made in the past to avoid the inevitable production of halohydrocarbons in the synthesis of alkylphosphonic esters. Thus, according to BE-A 803 856, a phosphite

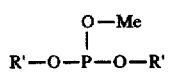

where R' is a relatively long-chain radical and Me is methyl, can be subjected to a rearrangement reaction in the presence of a catalytic amount of methyl iodide to give a phosphonic ester, but the methyl group always migrates to the phosphorus, ie. phosphonic esters of the type

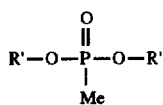

are obtained.

Instead of the organic halides, which are usually prepared from the corresponding alcohols or esters of organic acids, it is furthermore desirable to use these alcohols or esters directly.

It is an object of the present invention to prepare the compounds I in a technically simpler and more economical manner than in the past.

We have found that this object is achieved by a process for the preparation of phosphonic esters of the formula I where A is an aromatic radical or an α, β-olefinically unsaturated group and $R^1$ is $C_1$–$C_4$-alkyl or phenyl, wherein a phosphite of the formula II

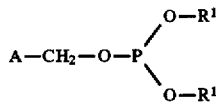

is subjected to a rearrangement reaction in the presence of a catalytic amount of a halide ion-donating compound (III) to give I.

The starting compounds II are known or are obtainable in a manner known per se, particularly advantageously by reacting a phosphite of the formula IV

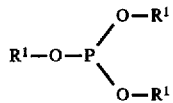

with an alcohol or ester of the general formula V

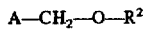

where $R^2$ is hydrogen, $C_1$–$C_4$-alkylcarbonyl, preferably acetyl, or benzoyl, in the presence of a base to give II.

If A is an α, β-olefinically unsaturated group, the starting compounds V are generally alcohols or esters having the allyl alcohol structure.

With regard to the particularly desirable products I, preferred radicals A are those of the formula VI

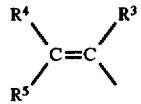

where
$R^3$ is hydrogen or $C_1$–$C_4$-alkyl and $R^4$ and $R^5$ are each hydrogen, alkyl, alkenyl, aryl, hetaryl, dialkoxymethyl or alkoxycarbonyl.

Particularly important compounds of the formula V are 3-(5,5-dimethyl-1,3-dioxan-2-yl)-2-butenol

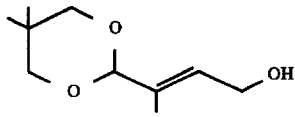

3-(5,5-dimethyl-1,3-dioxan-2-yl)-2-methylpropenol

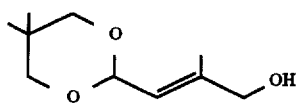

and geraniol

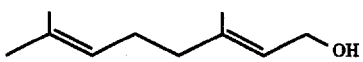

If A is an aromatic radical, the alcohols or esters are derived from benzyl alcohol. Phenyl and a halogen-, alkoxy-, alkyl- or perfluoroalkyl-substituted phenyl group are particularly important as radicals A.

Particularly suitable phosphites of the general formula IV which are used for the transesterification are those which are derived from readily volatile alcohols, ie. preferably trimethyl phosphite and triethyl phosphite. The commercially available triphenyl phosphite is also suitable for the transesterifications.

In order to suppress polytransesterifications, the phosphite is used with the compound V in a molar ratio of from 1:1 to 3:1, preferably from 1:1 to 2:1.

In the preparation of II, tertiary a/nines, alkaline earth metal hydroxides and especially alkali metal hydroxides may advantageously be used as bases. Alkali metal and alkaline earth metal alcoholates are also suitable, those of the $C_1$–$C_4$- alkanols being particularly suitable. The bases are preferably used in an amount of from 1 to 100, preferably from 20 to 100, mol %, based on the amount of II.

The reactions for the preparation of II and I can be carried out in the presence of a polar solvent, such as dimethylformamide, or of an alkanol, in particular a $C_1$–$C_4$- alkanol. In some cases, water is also suitable. However, the reactions are preferably carried out in the absence of a solvent.

The mixed phosphorous ester II formed in the reaction can be isolated or can advantageously be converted, without isolation, directly into the phosphonic ester I. In the case of the last-mentioned reaction, catalytic amounts of a halide ion-donating compound III are present. Particularly suitable halide ion-donating compounds III are iodine compounds, such as alkali metal and alkaline earth metal iodides, especially lithium iodide, and elemental iodine. The corresponding chlorides and bromides are also suitable. The amount of compounds III is preferably from 0.01 to 10, in particular from 0.1 to 5, mol %, based on the amount of II.

The reaction is advantageously carried out at elevated temperatures, preferably at from 80° to 160° C., resulting in reaction times of from 0.5 to 16, as a rule from 1 to 10, hours. Alcohol formed from the phosphite IV used, or the carboxylate of said alcohol, can be distilled off provided that these compounds are readily volatile. The crude product can be purified by known methods, preferably by fractional distillation, in particular under reduced pressure.

Examples 1–11 a) Preparation of phosphonic esters I via isolated mixed phosphorous esters II

1. Preparation of the mixed phosphorous ester

A mixture of 1 mol of alcohol or ester V, 2 mol of triethyl phosphite IV and 30 mmol of potassium tert-butylate (where an a is used) or 50 m mol of sodium methylate (where an ester is used) was first heated to 90° C. and then, in the course of 3 hours, to 140° C. Ethanol and ethyl acetate began to distill off. Excess triethyl phosphite was separated off by distillation in the course of 2 hours at 120° C./15 mbar, after which the phosphite II was purified by fractional distillation.

2. Rearrangement of the phosphite to give the phosphonic ester A mixture of 1 mol of phosphite II from stage 1 and 10 mmol of lithium iodide or 1 mmol of iodine was heated for 2 hours at 140° C. The phosphonic ester I was obtained by fractional distillation.

b) Preparation of I starting from phosphite IV

A mixture of 1 mol of alcohol or ester V, 2 mol of triethyl phosphite, 30 mmol of potassium tert-butylate and 10 mmol of lithium iodide was heated to 90° C. Ethanol began to distill off. The temperature was brought to the final temperature of 140° C. in the course of three hours by increasing the temperature by 10° C. every half hour. Thereafter, excess triethyl phosphite was distilled off and the residue was then heated for three hours at 140° C. The product was obtained by fractional distillation.

The details of these experiments and the results thereof are shown in the table below.

TABLE

| Example | Alcohol or Ester V | Process | Yield of II in mol %, based on V | Phosphonic ester I | Yield of I in mol %, based on V |
|---|---|---|---|---|---|
| 1 | (structure) | a | 81 | (structure) Bp. 125–132° C./0.4 mbar | 64 |
| 2 | (structure) | a | 81 | | 60 |

TABLE-continued

| Example | Alcohol or Ester V | Process | Yield of II in mol %, based on V | Phosphonic ester I | Yield of I in mol %, based on V |
| --- | --- | --- | --- | --- | --- |
| 3 | ![structure] | b | | | 65 |
| 4 | ![structure] | a | 63 | ![structure] Bp. 125–132° C./0.4 mbar | 47 |
| 5 | ![structure] | a | | | 65 |
| 6 | ![structure] | a | | | 70 |
| 7 | ![structure] | a | 68 | | 54 |
| 8 | MeO-C₆H₄-CH₂OH | a | 74 | | 72 |
| 9 | tert.-BuO-C₆H₄-CH₂OH | a | 68 | | 53 |
| 10 | Cl-C₆H₄-CH₂OH | a | 72 | | 66 |
| 11 | F₃C-C₆H₄-CH₂OH | a | 56 | | 54 |

We claim:

1. A process for the preparation of a phosphonic ester of the formula I

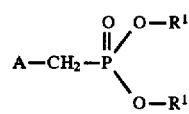   I where A is an aromatic radical or an , -olefinically unsaturated group and $R^1$ is $C_1$-$C_4$- alkyl or phenyl, wherein a phosphite of the formula II

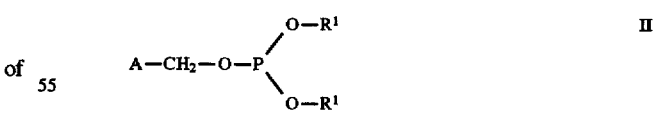

is subjected to a rearrangement reaction in the presence of a catalytic amount of a halide ion-donating compound to give I.

2. A process for the preparation of a phosphonic ester I as defined in claim 1, wherein a phosphite of the formula IV

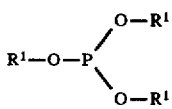   IV is reacted with an alcohol or ester of the formula V

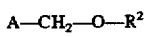  V where $R^2$ is hydrogen, $C_1$–$C_4$-alkylcarbonyl or benzoyl, in a molar ratio of from 1:1 to 3:1 mol phosphite to alcohol or ester of the formula V, in the presence of a base to give II, and the latter, without being isolated from the reaction mixture, is subjected to a rearrangement reaction with the aid of a catalytic amount of a halide ion-donating compound to give I.

3. A process as defined in claim 1, in which A is a group of the formula VI

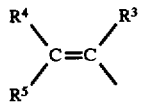  VI where $R^3$ is hydrogen or $C_1$–$C_4$-alkyl and $R^4$ and $R^5$ are each hydrogen, alkyl, alkenyl, aryl, hetaryl, dialkoxymethyl or alkoxycarbonyl.

4. A process as defined in claim 1, in which $R^1$ is ethyl.

5. A process as defined in claim 1, wherein the halide ion-donating compound is an iodine ion-donating compound.

6. A process as defined in claim 5, wherein the iodide ion-donating compound is an alkali metal iodide or iodine.

7. A phosphonic ester of the formula

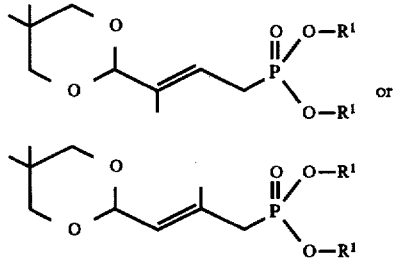

where $R^1$ is $C_1$–$C_4$-alkyl or phenyl.

* * * * *

UNITED STATES PATENT AND TRADEMARK OFFICE
CERTIFICATE OF CORRECTION

PATENT NO.: 5,679,804

DATED: October 21, 1997

INVENTOR(S): DITRICH et al.

It is certified that error appears in the above-identified patent and that said Letters Patent is hereby corrected as shown below:

Column 5, claim 1, line 65, "an , -olefinically" should be --an $\alpha,\beta$-olefinically--.

Signed and Sealed this

Ninth Day of December, 1997

*Attest:*

BRUCE LEHMAN

*Attesting Officer*     *Commissioner of Patents and Trademarks*